United States Patent
Wang et al.

(10) Patent No.: US 11,517,507 B2
(45) Date of Patent: Dec. 6, 2022

(54) PREPARATION METHOD FOR DENTAL MATERIAL WITH TRANSMITTANCE AND COLOR GRADIENTS AND PRODUCT PREPARED THEREBY

(71) Applicant: LIAONING UPCERA CO., LTD, Liaoning (CN)

(72) Inventors: Hongjuan Wang, Liaoning (CN); Feng Shi, Liaoning (CN); Jiahang Wu, Liaoning (CN)

(73) Assignee: LIAONING UPCERA CO., LTD, Liaoning (CN)

(*) Notice: Subject to any disclaimer, the term of this patent is extended or adjusted under 35 U.S.C. 154(b) by 396 days.

(21) Appl. No.: 16/650,269

(22) PCT Filed: May 16, 2018

(86) PCT No.: PCT/CN2018/087109
§ 371 (c)(1),
(2) Date: Mar. 24, 2020

(87) PCT Pub. No.: WO2019/062144
PCT Pub. Date: Apr. 4, 2019

(65) Prior Publication Data
US 2020/0268616 A1    Aug. 27, 2020

(30) Foreign Application Priority Data

Sep. 30, 2017 (CN) .......................... 201710923133.X

(51) Int. Cl.
| | |
|---|---|
| A61K 6/78 | (2020.01) |
| A61K 6/15 | (2020.01) |
| A61K 6/77 | (2020.01) |
| A61K 6/887 | (2020.01) |
| A61K 6/76 | (2020.01) |
| B29B 7/90 | (2006.01) |
| B29C 43/00 | (2006.01) |
| B29C 43/52 | (2006.01) |
| B29K 105/00 | (2006.01) |

(52) U.S. Cl.
CPC .................. *A61K 6/15* (2020.01); *A61K 6/76* (2020.01); *A61K 6/77* (2020.01); *A61K 6/78* (2020.01); *A61K 6/887* (2020.01); *B29B 7/90* (2013.01); *B29C 43/003* (2013.01); *B29C 43/52* (2013.01); *B29K 2105/0002* (2013.01)

(58) Field of Classification Search
CPC ...................................................... A61K 6/78
See application file for complete search history.

(56) References Cited

U.S. PATENT DOCUMENTS

| | | | |
|---|---|---|---|
| 4,440,878 A | 4/1984 | Kawahara et al. | |
| 5,990,195 A | 11/1999 | Arita | |
| 10,219,880 B2 | 3/2019 | Rolf et al. | |
| 10,485,736 B2 | 11/2019 | Wang et al. | |
| 2008/0319104 A1 | 12/2008 | Klapdohr et al. | |
| 2013/0277873 A1 | 10/2013 | Sadoun | |
| 2016/0228222 A1 | 8/2016 | Rolf et al. | |
| 2018/0161251 A1 | 6/2018 | Wang et al. | |
| 2018/0221250 A1 | 8/2018 | Qiu et al. | |

FOREIGN PATENT DOCUMENTS

| | | |
|---|---|---|
| CN | 101244013 A | 8/2008 |
| CN | 101518499 A | 9/2009 |
| CN | 102228408 A | 11/2011 |
| CN | 102285795 A | 12/2011 |
| CN | 102344285 A | 2/2012 |
| CN | 102579148 A | 7/2012 |
| CN | 105362084 A | 3/2016 |
| CN | 105705112 A | 6/2016 |
| CN | 107537061 A | 1/2018 |
| EP | 3 287 118 A1 | 2/2018 |
| JP | H10-323353 A | 12/1998 |
| JP | 2004-035332 A | 8/2005 |
| KR | 20180014430 A | 2/2018 |
| KR | 20180023891 A | 3/2018 |
| WO | WO 2017/080092 A1 | 5/2017 |
| WO | WO 2017/219742 A1 | 12/2017 |

OTHER PUBLICATIONS

Korean Patent Office, Notice of Allowance in Korean Patent Application No. 10-2020-7012478 (dated Jul. 29, 2021).
State Intellectual Property Office of the People's Republic of China, International Search Report in International Application No. PCT/CN2018/087109 (dated Aug. 8, 2018).
State Intellectual Property Office of the People's Republic of China, Written Opinion in International Application No. PCT/CN2018/087109 (dated Aug. 8, 2018).
International Bureau of WIPO, International Preliminary Report on Patentability in International Application No. PCT/CN2018/087109 (dated Mar. 31, 2020).

(Continued)

*Primary Examiner* — Benjamin J Packard

(74) *Attorney, Agent, or Firm* — Leydig, Voit & Mayer, Ltd.

(57) ABSTRACT

Disclosed are a dental material with transmittance and color gradients and a method of preparing the dental material. The method includes (1) preparing at least three types of composite resin material precursor powders; (2) sequentially adding the precursor powders into a mold and performing dry pressing to obtain a preform body; alternatively, (2') dry pressing the first type of precursor powder into a first green body, wrapping the first green body with the second type of precursor powder and then performing dry pressing to obtain a second green body, and repeating the wrapping and dry pressing operations until all types of precursor powder are dry pressed to obtain a preform body; and (3) performing hot-pressing consolidation on the preform body to obtain the desired dental material.

14 Claims, No Drawings

(56) References Cited

OTHER PUBLICATIONS

Japan Patent Office, Office Action in Japanese Patent Application No. 2020-517809 (dated Mar. 23, 2021).
IP Australia, Examination Report in Australian Patent Application No. 2018340731 (dated Jan. 20, 2021).
European Patent Office, Extended European Search Report in European Patent Application No. 18861418.4 (dated Sep. 23, 2020).

PREPARATION METHOD FOR DENTAL MATERIAL WITH TRANSMITTANCE AND COLOR GRADIENTS AND PRODUCT PREPARED THEREBY

The present application is the U.S. national phase of International Application No. PCT/CN2018/087109, filed on May 16, 2018, which claims the priority of Chinese patent application No. 201710923133.X, with the title of "Preparation method for dental material with transmittance and color gradients and product prepared thereby", filed on Sep. 30, 2017 before the China National Intellectual Property Administration, the disclosures of which are incorporated herein by reference in their entireties for all purposes.

TECHNICAL FIELD

The present application relates to the field of dental restoration technology, and in particular relates to a method for preparing a dental material with light transmittance and color gradients and a product prepared thereby.

BACKGROUND OF THE INVENTION

With the advancement of dental technology, CAD/CAM technology has also been used in the field of dental technology. The dental chair-side CAD/CAM technology is a technology that putting a Computer Aided Design and Computer Aided Manufacture device at the side of dental chair, obtaining the tooth model of patient through digital technology after the doctor completes tooth preparation and the other treatments, then analyzing the data, and designing and manufacturing the dental prosthesis (restoration) by computer. With chair-side CAD/CAM technology, the manufacture of restoration can be completed in one-step. Thus, the temporary restoration is not necessary, saving time for patient, and significantly improving the precision and accuracy of the restoration, improving the success rate of restoration treatment. The gingiva discoloration and marginal unfitness of conventional PFM (Porcelain Fused to Metal) denture and removable denture can be reduced effectively, and the patient's satisfaction for the treatment can be improved significantly. The development of the dental chair-side CAD/CAM also drives the development of the related material. At present, the commonly used composite materials mainly include: composite resin, resin-permeable ceramic composite materials, polyetheretherketone (PEEK) materials, and the like. Through CAD/CAM technology, restorations made of composite resin materials can meet the requirements of precision manufacture and efficiency of restorations in the dental field. However, since the existing composite resins are all monochromatic materials with a single light transmittance, the color and light transmittance of the entire restoration produced are the same. This is obviously not enough for the aesthetic effect of natural tooth. Natural tooth is composed of enamel and dentin. The origin and characteristics of the two tissues are completely different, and they have their own unique optical characteristics. Dentin constitutes the body of the tooth and has light-blocking property. The enamel covers the dentin and has translucency and light transparency. This results in the light transmittance and color of natural tooth gradually varying from the neck part of the tooth to the incisal part of the tooth. Compared with natural tooth, the restoration made of composite resin materials with a single aesthetic effect has the disadvantages of low similarity in the gradient light transmittance and color with nature tooth.

At present, Shenzhen UPCERA Dental Technology Co., Ltd has filed a patent application related to polymer materials for CAD/CAM in China (application number: CN105362084A: Multilayer-color composite material for use in dental department, and preparation method therefor), which provides a method for preparing a composite resin material with multi-layer color. The multi-layer composite resin material comprises at least three layers of composite resin material with different colors, that is, composite resin material with the same light transmittance. After superimposing the composite resin material of each layer, the color of composite resin material of each layer varies from the bottom layer to the top layer in turn, thereby imitating the color of natural tooth. However, it fails to reflect the characteristic of light transmittance gradient of natural tooth. In addition, the existing composite resin material with multi-layer color has the disadvantage of low strength.

SUMMARY OF THE INVENTION

In view of this, the purpose of the present application is to provide a method for preparing a dental material with light transmittance and color gradients and a product prepared thereby, so as to achieve the purpose of improving the aesthetic effect and strength of the composite resin material. The specific technical solutions are as follows.

The present application provides a method for preparing a dental material with light transmittance and color gradients, comprising:

(1) preparing at least three kinds of composite resin material precursor powders with different light transmittances, wherein each composite resin material precursor powder is prepared by: weighing raw materials, including a resin monomer, a filler, an initiator and a colorant, and mixing the raw materials to obtain a composite resin material precursor powder, wherein the weight ratio of the filler to the resin monomer is 10:90 to 90:10, preferably 70:30 to 85:15, the initiator is present in an amount of 0.1 to 3%, preferably 0.1 to 2% by weight of the resin monomer, the colorant is present in an amount of 0.001 to 0.2%, preferably 0.002 to 0.1% by weight of the total resin monomer and the filler; and the resin monomer includes olefinic unsaturated monomers and/or epoxy resins;

(2) adding successively the at least three kinds of composite resin material precursor powders with different light transmittances to a mold in an ascending order of light transmittance or in an descending order of light transmittance, and molding by dry-pressing under a pressure of 3 to 20 MPa, preferably under a pressure of 4 to 10 MPa, to obtain a pre-molding green body of dental material with light transmittance and color gradients; wherein, a top surface of the precursor powder is flattened after adding each composite resin material precursor powder into the mold;

or (2') among the at least three kinds of composite resin material precursor powders with different light transmittances, molding by dry-pressing a first composite resin material precursor powder under a pressure of 3 to 20 MPa, preferably 4 to 10 MPa to obtain a first green body; coating the first green body with a second composite resin material precursor powder, molding by dry-pressing under a pressure of 3 to 20 MPa, preferably 4 to 10 MPa to obtain a second green body; and repeating the operations of coating and molding by dry-pressing until the at least three kinds of composite resin material precursor powder are molded by dry-pressing to obtain a pre-molding green body of dental material with light transmittance and color gradients, wherein the light transmittance of each layer of precursor powder in the pre-molding green body of dental material with light transmittance and color gradients is increased successively from inside to outside;

(3) subjecting the pre-molding green body of dental material with light transmittance and color gradients prepared in step (2) or step (2') to a thermocuring treatment to obtain the dental material with light transmittance and color gradients, wherein the thermocuring treatment is performed at a temperature of 115 to 185° C., preferably 131 to 171° C., under a pressure of greater than 160 MPa, preferably 160 to 300 MPa, more preferably 200 to 250 MPa for a time period of 0.5 to 4 h, preferably 0.5 to 3 h.

Optionally, the dental material with light transmittance and color gradients further has a multi-layer color, and a chrominance difference between two adjacent layers of the composite resin materials is greater than or equal to 1 and less than or equal to 11 based on the Lab color system.

The maximum value of a chrominance difference between non-adjacent layers of the composite resin materials in the dental material with light transmittance and color gradients is greater than or equal to 2 and less than or equal to 15 based on the Lab color system.

The difference between the sum of chrominance differences between all adjacent layers of composite resin materials in the dental material with light transmittance and color gradients and the chrominance difference between the layers of composite resin materials with a highest chrominance and a lowest chrominance in the dental material with light transmittance and color gradient is not more than 2;

wherein, an equation for calculating the chrominance difference based on the Lab color system is $\Delta E=\sqrt{\Delta L^2+\Delta a^2+\Delta b^2}$, wherein $\Delta E$ is a chrominance difference; $\Delta L$ is a difference of L values between two layers; $\Delta a$ is a difference of a values between two layers; and $\Delta b$ is a difference of b values between two layers.

Optionally, the dental material with light transmittance and color gradients also has a multi-layer light transmittance, wherein a difference between the light transmittances of two adjacent layers of the dental material with light transmittance and color gradients is 0.5 to 10%; a difference between the light transmittance of two non-adjacent layers of composite resin material is 1 to 15%; and a visible-light (wavelength of 550 nm) transmittance of a layer of composite resin material with a highest light transmittance is 50 to 75%, a light transmittance of a layer of composite resin material with a lowest light transmittance is 30 to 60%, and a light transmittance of other layers of the composite resin material between the layer of composite resin material with a highest light transmittance and the layer of composite resin material with a lowest light transmittance is 40 to 70%.

Optionally, the weight ratio of the filler to the resin monomer is 31:69 to 69:31, preferably 43:57 to 62:38, the initiator is present in an amount of 0.1 to 3%, preferably 0.1 to 2% by weight of the resin monomer, the colorant is present in an amount of 0.001 to 0.2%, preferably 0.002 to 0.1% by weight of the total resin monomer and the filler.

The thermocuring treatment is performed at a temperature of 115 to 169° C., preferably 155 to 165° C., under a pressure of 210 to 300 MPa, preferably 240 to 290 MPa, for a time period of 1.1 to 1.8 h, preferably 1.6 to 1.8 h.

Optionally, mixing raw materials to obtain the composite resin material precursor powder comprises:

mixing the raw materials with a ball milling additive and ball milling for 0.5 to 2 h to obtain the composite resin material precursor powder, wherein the mass ratio of the raw materials:grinding balls:ball milling additive is (1:1:1) to (3:6:2), preferably 2:4:1.

Optionally, the particle size of the filler is not more than 2.5 μin, preferably not more than 2 μin, and more preferably 0.05 to 2 μin; and the refractive index of the filler is 1.40 to 1.7, preferably 1.45 to 1.6.

Optionally, the raw materials further comprise a polymerization inhibitor, and the polymerization inhibitor accounts for 0.1 to 3%, preferably 0.2 to 2% by weight of the resin monomer.

Optionally, the raw materials further comprise a promoter, and the promoter accounts for 0.1 to 3%, preferably 0.2 to 2% by weight of the resin monomer.

Optionally, the raw materials further comprise at least one of a fluorescent agent, an indicator, an inhibitor, an accelerator, a viscosity modifier, a wetting agent, an antioxidant, a surfactant, a stabilizer, and a diluent.

Optionally, the filler may further comprise nanoparticle, wherein the nanoparticle accounts for 1 to 25%, preferably 1 to 15% by weight of the filler; and the average diameter of the nanoparticle is 35 to 100 nm, preferably 40 to 50 nm.

Optionally, the raw materials further include reinforcing fibers, and the reinforcing fibers account for 1 to 30%, preferably 1 to 10% by weight of the filler; the diameter of the reinforcing fibers is 0.1 to 25 μm, preferably 0.5 to 10 μm; the length of the reinforcing fiber is 0.001 to 1 mm, preferably 0.1 to 0.5 mm; the refractive index of the reinforcing fiber is 1.4 to 1.7, preferably 1.45 to 1.6; the reinforcing fiber includes any one of glass fiber, quartz fiber, silicon fiber, ceramic fiber, and polymer fiber, or a combination thereof, and the polymer fiber is preferably a polyethylene fiber.

Optionally, mixing raw materials to obtain the composite resin material precursor powder comprises:

mixing the resin monomer, filler, initiator and colorant other than the reinforcing fibers, and ball milling for 0.5-2 h to obtain a mixture of raw materials, wherein the mass ratio of raw materials:grinding balls:ball milling additives is 1:1:1 to 3:6:2, preferably 2:4:1; and mixing the mixture of raw materials with the reinforcing fibers to obtain the composite resin material precursor powder.

Optionally, the colorant includes any one of a red colorant, a yellow colorant, and a black colorant, or a combination thereof, wherein the red colorant accounts for 0.001 to 0.06% by weight of the raw material, and is preferably iron oxide red; the yellow colorant accounts for 0.001 to 0.04% by weight of the raw materials, and includes any one of iron oxide yellow, bismuth yellow, vanadium zirconium yellow, and cerium praseodymium yellow, or a combination thereof; and the black colorant accounts for 0 to 0.03% by weight of the raw materials, and is preferably iron oxide black.

The present application also provides a dental material with light transmittance and color gradients produced by the above methods.

The dental material with light transmittance and color gradients prepared by the method provided by the present application has the following beneficial effects:

(1) The dental material with light transmittance and color gradients prepared by the method provided by the present application has an extremely high flexural strength. After experimental measurement, the flexural strength reaches more than 248 MPa.

(2) The dental material with light transmittance and color gradients prepared by the method provided by the present application has an extremely high compressive strength. After experimental measurement, the compressive strength reaches more than 581 MPa.

(3) The dental material with light transmittance and color gradients prepared by the method provided by the present application can effectively improve the aesthetic effect of the restoration, so that the dental material has gradients color and transparency in the height direction, and can better simulate the aesthetic characteristics of the neck part and incisal part of natural tooth.

Of course, the implementation of any product or method of this application does not necessarily need to achieve all the advantages described above at the same time.

DETAILED DESCRIPTION OF THE INVENTION

The examples of the present application provide a method for preparing a dental material with light transmittance and color gradients, comprising the following steps.

Step (1) preparing at least three kinds of precursor powder of composite resin material with different light transmittances, wherein each precursor powder of composite resin material is prepared by: weighing raw materials, including a resin monomer, a filler, an initiator and a colorant; and mixing the raw materials to obtain the precursor powder of composite resin material, wherein a weight ratio of the resin monomer to the filler is 10:90 to 90:10, preferably 70:30 to 85:15, the initiator is present in an amount of 0.1 to 3%, preferably 0.1 to 2% by weight of the resin monomer, the colorant is present in an amount of 0.001 to 0.2%, preferably 0.002 to 0.1% by weight of the total resin monomer and the filler, and the resin monomer includes olefinic unsaturated monomers and/or epoxy resins.

In practical applications, the resin monomer can be selected from polymerizable, olefinic unsaturated monomers with or without acid functional groups, such as any one of acrylates, methacrylates, hydroxylated acrylates, hydroxylated methacrylates, or a combination thereof.

The resin monomer can also be selected from polymerizable resinized monomers other than methacrylates, for example epoxy resins, such as any one of polyethylene glycol dimethacrylate (PEGDMA), bisphenol A-glycidyl dimethacrylate (Bis-GMA), urethane dimethacrylate (UDMA), triethylene glycol dimethacrylate (TEGDMA), bisphenol A-ethoxy dimethacrylate (Bis-EMA6), hydroxyethyl methacrylate (HEMA), bisphenol A-epoxy resin (epoxy resin E-44), or a combination thereof. The refractive indexes of the above materials used in the examples of the present application are close to that of natural tooth, allowing improving the aesthetic effect of the prepared dental material.

It should be noted that the resin monomer may also be a mixture of an olefinic unsaturated monomer and an epoxy resin. Generally, the epoxy resin can be 5% to 30% by weight of the olefinic unsaturated monomer.

For example, a resin monomer can be obtained according to the following formulation:
Bis-GMA: 0-70%, preferably 0-30%;
UDMA: 10-70%, preferably 40-60%;
Bis-EMA6: 0-50%, preferably 0-30%;
Epoxy resin E-44: 0-40%, preferably 0-20%;
TEGDMA: 10-60%, preferably 20-40%;
HEMA: 0-50%, preferably 0 -20%.

In one specific embodiment of the present application, the particle size of the filler is not more than 2.5 μm, preferably not more than 2 μm, and more preferably 0.05 to 2 μm; and the refractive index of the filler is 1.40 to 1.7, preferably 1.45 to 1.6.

In practical applications, the filler may also have a certain particle size graduation, for example, a part of the filler has a particle size range of 0.1 to 1 μm, and another part of the filler has a particle size range of less than 0.1 μm. The filler having a certain particle size graduation can give dental materials with light transmittance and color gradients better polishability and abrasion resistance.

It can be understood that the ratio of the fillers having different particle size can be determined according to the actual situation, which is not limited by the examples of the present application. The filler can be an inorganic material, including but not limited to: quartz powder, barium glass powder, lanthanum glass powder, borosilicate glass powder, silicon oxide-zirconium oxide composite powder, silicon oxide-ytterbium oxide composite powder, nano-silicon oxide powder, nano-zirconium oxide powder, nano-titanium oxide powder. The filler can also be an organic filler, including but not limited to polycarbonate powder, polyepoxide powder, polymerized methacrylics powder filled with inorganic materials; and polycarbonate powder, polyepoxide powder, polymerized methacrylics powder not filled with inorganic materials.

The initiator includes but not limited to any one of dicumyl peroxide, tert-butyl peroxide, benzoyl peroxide, tert-butyl peroxyacetate, tert-butyl peroxybenzoate, or a combination thereof.

In the specific embodiment of the present application, in order to improve the bonding strength between the filler and the monomer of polymerization, the filler is surface-modified with a coupling agent before being mixed with other raw materials. The coupling agent that can be used includes but not limited to γ-methacryloyloxypropyl trimethoxysilane KH-570, γ-mercaptopropyl triethoxysilane KH-580, γ-aminopropyl trimethoxysilane JH-A111 and the like. The surface treatment of the filler using a coupling agent can enhance the bonding strength between the filler particles and the monomer of polymerization, such as olefinic unsaturated monomers, thereby improving the hardness of the restoration.

In one specific embodiment of the present application, the step of mixing the raw materials to obtain the precursor powder of composite resin material comprises: mixing the raw materials with a ball milling additive, and ball milling for 0.5 to 2 h to obtain the precursor powder of composite resin material, wherein the mass ratio of the raw materials: grinding balls:ball milling additive is (1:1:1) to (3:6:2), preferably 2:4:1.

Specifically, the processing conditions of ball milling can be: using agate or zirconium oxide grinding balls, and the ball milling additive is a volatile organic substance, such as any one of methanol, ethanol and acetone, or a combination thereof. Then, the mixture obtained by ball milling is subjected to a rotary evaporation and drying process to prepare a precursor powder of composite resin material with light transmittance and color gradients, wherein the temperature of the rotary evaporation is 20 to 100° C., preferably 30 to 80° C., and more preferably 45 to 58° C., and the temperature during drying is 20 to 100° C., preferably 30 to 80° C., and more preferably 45 to 58° C.

The precursor powder of composite resin material prepared according to the above-mentioned ball milling method can make each component in the precursor powder of composite resin material more uniformly mixed, improve the preparation efficiency, and is beneficial to the molding of material.

It can be understood that the ratio of the resin monomer, the filler, the initiator, and the colorant in each composite resin material can be adjusted according to the actual requirements, so as to obtain composite resin materials with different light transmittances.

Step (2) adding successively the at least three kinds of precursor powder of composite resin material with different light transmittances to the mold in an ascending order of light transmittance or in an descending order of light transmittance, molding by dry-pressing under a pressure of 3 to 20 MPa, preferably under a pressure of 4 to 10 MPa, to obtain a pre-molding green body of dental material with light transmittance and color gradients; wherein, flattening a top surface of the precursor powder after each precursor powder of the composite resin material is added to the mold.

Exemplarily, a composite resin material precursor powder A has a light transmittance of 50 to 75%; a composite resin material precursor powder B has a light transmittance of 40 to 70%; and a composite resin material precursor powder C has a light transmittance of 30 to 60%, wherein the light transmittance is measured by a light transmittance tester at a test light wavelength of 550 nm.

In practical applications, the first method for obtaining a composite resin material precursor powder with a specific light transmittance is: preparing composite resin material precursor powder of multiple formulations, and then curing the prepared precursor powder under preset conditions. After curing, the light transmittances of the multiple composite resin material precursor powders are measured by a light transmittance tester at a test light wavelength of 550 nm. Then the corresponding formulation of the restoration precursor powder is selected according to the required light transmittance, and the composite resin material precursor powder is prepared according to the formulation. The second method is: using the empirical equation to calculate the light transmittance corresponding to each composite resin material precursor powder according to the properties and proportions of each component in the composite resin material precursor powder, and then selecting corresponding formulation of the restoration precursor powder according to the required light transmittance. Then the composite resin material precursor powder is prepared according to the formulation. The above two methods for obtaining a composite resin material precursor powder with a specific light transmittance are the prior art, and are not repeated herein.

In the specific embodiments, in ascending order of the light transmittance, adding the above composite resin material precursor powder C to a mold, and flattening a top surface of the precursor powder C; then adding the above composite resin material precursor powder B to the mold, and flattening a top surface of the precursor powder B; then adding the above composite resin material precursor powder A to the mold, and flattening a top surface of the precursor powder A; molding by dry-pressing at a pressure of 3 to 20 MPa, preferably 4 to 10 MPa to obtain a pre-molding green body of dental material with light transmittance and color gradients;

Alternatively,

Step (2') for the three kinds of monochrome composite resin material precursor powder with different light transmittances, molding by dry-pressing a composite resin material precursor powder C under a pressure of 3 to 20 MPa, preferably 4 to 10 MPa to obtain a first green body; coating the first green body with a composite resin material precursor powder B; molding by dry-pressing under a pressure of 3 to 20 MPa, preferably 4 to 10 MPa to obtain a second green body; and repeating the operations of coating and molding by dry-pressing until the three kinds of composite resin material precursor powder are molded by dry-pressed to obtain a pre-molding green body of dental material with light transmittance and color gradients, wherein the light transmittance of each layer of precursor powder in the pre-molding green body of dental material with light transmittance and color gradients increases successively from inside to outside;

Step (3) subjecting the pre-molding green body of dental material with light transmittance and color gradients prepared in step (2) or step (2') to a thermocuring treatment to obtain a dental material with light transmittance and color gradients, wherein the thermocuring treatment is performed at a temperature of 115 to 185° C., preferably 131 to 171° C., under a pressure of greater than 160 MPa, preferably 160 to 300 MPa, more preferably 200 to 250 MPa for a time period of 0.5 to 4 h, preferably 0.5 to 3 h.

In one specific embodiment of the present application, the initiator of thermocuring is any one of dicumyl peroxide, t-butyl peroxide, benzoyl peroxide, t-butyl peroxyacetate, t-butyl peroxybenzoate, or a combination thereof.

In one specific embodiment of the present application, the chrominance difference between two adjacent layers of the composite resin material precursor powder in the pre-molding green body of dental material with light transmittance and color gradients is greater than or equal to 1 and less than or equal to 11, based on the Lab color system.

The maximum value of the chrominance difference between non-adjacent layers of the composite resin material in the pre-molding green body of dental material with light transmittance and color gradients is greater than or equal to 2 and less than or equal to 15, based on the Lab color system.

The difference between the sum of chrominance difference between all adjacent layers of composite resin materials in the dental material with light transmittance and color gradients and the chrominance difference between the layer of composite resin material with a highest chrominance and the layer of composite resin material with a lowest chrominance in the dental material with light transmittance and color gradients is not more than 2;

wherein, the equation for calculating the chrominance difference based on the Lab color system is $\Delta E=\sqrt{\Delta L^2+\Delta a^2+\Delta b^2}$, and $\Delta E$ is the chrominance difference; $\Delta L$ is a difference of L values between the two layers; $\Delta a$ is a difference of a values between the two layers; and $\Delta b$ is a difference of b values between the two layers.

In one specific embodiment, the dental material with light transmittance and color gradients also has a multi-layer light transmittance. A difference of the light transmittance between two adjacent layers of the dental material with light transmittance and color gradients is 0.5 to 10%; a difference of the light transmittance between two non-adjacent layers of composite resin material is 1 to 15%; and a light transmittance of a layer of composite resin material with a highest light transmittance is 50 to 75%, a light transmittance of a layer of composite resin material with a lowest light transmittance is 30 to 60%, and a light transmittance of other layers of the composite resin material between the layer of composite resin material with a highest light transmittance and the layer of composite resin material with a lowest light transmittance is 40 to 70%.

In practical applications, a composite resin material with high translucency can simulate the incisal part of the tooth; a composite resin material with moderate translucency belongs to a transition layer, which can be one layer or multiple layers; and a composite resin material with low translucency can simulate neck part of the tooth.

Specifically, by taking the dental material with gradient light transmittance from top to bottom and gradient color prepared by following three composite resin material precursor powders as an example, the requirements of chrominance difference among the three composite resin material precursor powders are described.

The term of "chrominance difference" herein is sometimes also referred to as "color difference".

The chrominance of the three composite resin precursor powders is measured by using a colorimeter or a spectrophotometer, based on the Lab color system. For example, L1, a1, b1 can be used to indicate the chrominance of the first composite resin material precursor powder; L2, a2, b2 can be used to indicate the chrominance of the second composite resin material precursor powder; and L3, a3, b3 can be used to indicate the chrominance of the third composite resin material precursor powder.

According to the chrominance of each precursor powders above, a formula of $\Delta E=\sqrt{\Delta L^2+\Delta a^2+\Delta b^2}$ can be used to calculate the chrominance difference $\Delta E$ between layers, wherein $\Delta E$ is a chrominance difference; $\Delta L$ is a difference of L values between the two layers; $\Delta a$ is a difference of a values between the two layers; and $\Delta b$ is a difference of b values between the two layers.

If the first composite resin material precursor powder is used as the top layer material, the second composite resin material precursor powder is used as the intermediate transition layer material, and the third composite resin material precursor powder is used as the bottom layer material, and L1≥L2≥L3, a1<a2<a3, b1<b2<b3, that is, the L values of the first composite resin material precursor powder, the second composite resin material precursor powder and the third composite resin material precursor powder gradually decreases, and the a values and the b values of the first composite resin material precursor powder, the second composite resin material precursor powder and the third composite resin material precursor powder gradually increases, the characteristic of gradient light transmittance of natural tooth can be simulated.

In practical applications, the chrominance difference between the top layer and the bottom layer is 2 or more and 15 or less; the chrominance difference between the top layer and the intermediate transition layer is 1 or more and 11 or less; the chrominance difference between the intermediate transition layer and the bottom layer is 1 or more and 11 or less, and the absolute value of the chrominance difference between the top layer and the bottom layer minus the sum of the chrominance difference between the intermediate transition layer and the bottom layer and the chrominance difference between the top layer and the intermediate transition layer is 1 or less.

It is found through experiments that for the first composite resin material precursor powder, L1 is 62 to 80, a1 is −2.2 to 2.2, b1 is 5 to 16, and the light transmittance is 50% to 75%. For the second composite resin material precursor powder, L2 is 58 to 76, a2 is −2.0 to 2.5, b2 is 8 to 20, and the light transmittance is 40% to 70%. For the third composite resin material precursor powder, L3 is 53 to 72, a3 is −1.8 to 2.8, b3 is 10 to 24, and the light transmittance is 30% to 60%.

It can be understood that in the dental material with light transmittance and color gradients prepared by the above three composite resin material precursor powders, the light transmittance of the first composite resin material precursor powder as the top layer is higher than that of the second composite resin material precursor powder as the intermediate transition layer; and the light transmittance of the second composite resin material precursor powder as the intermediate transition layer is higher than that of the third composite resin material precursor powder as the bottom layer.

If the restoration is prepared by four or more composite resin material precursor powders, the chrominance difference between non-adjacent layers is 2 or more and 15 or less; the chrominance difference between two adjacent layers is 1 or more and 11 or less; in addition, when the light transmittance of the bottom layer of the restoration is the lowest, the light transmittance of each layer of the composite resin material is successively increased from the bottom layer to the top layer; or when the light transmittance of the top layer of the restoration is the lowest, the light transmittance of each layer of the composite resin material is successively decreased from the bottom layer to the top layer.

The dental material with light transmittance and color gradients from top to bottom prepared by using the composite resin material precursor powders having the above chrominance difference between layers can simulate the characteristic of light transmittance and color gradients from incisal part to neck part of the natural tooth, thereby making the dental restoration more beautiful.

Specifically, by further taking the other dental material with light transmittance and color gradients from inside to outside prepared by the above three composite resin material precursor powders as an example, the requirements of the chrominance difference among the three composite resin material precursor powders are described.

The first composite resin material precursor powder with chrominance values of L1, a1, b1 is used as the outermost layer material; the second composite resin material precursor powder with chrominance values of L2, a2, b2 is used as the secondary outer layer material; and the third composite resin material precursor powder with chrominance values of L3, a3, b3 is used as the innermost material.

In practical applications, the chrominance difference between the outermost layer and the innermost layer is 2 or more and 15 or less; the chrominance difference between the outermost layer and the secondary outer layer is 1 or more and 11 or less; the chrominance difference between the secondary outer layer and the innermost layer is 1 or more and 11 or less, and the absolute value of the chrominance difference between the outermost layer and the innermost layer minus the sum of the chrominance difference between the outermost layer and the secondary outer layer and the chrominance difference between the secondary outer layer and the innermost layer is 1 or less.

It can be understood that the light transmittance of the first composite resin material precursor powder as the outermost layer is higher than that of the second composite resin material precursor powder as the secondary outer layer; and the light transmittance of the second composite resin material precursor powder as the secondary outer layer is higher than that of the third composite resin material precursor powder as the innermost layer.

The dental material with light transmittance and color gradients from inside to outside prepared by using the composite resin material precursor powders having the above chrominance difference between layers can simulate the characteristic of light transmittance gradient from inside to outside of the natural tooth, thereby making the dental restoration more beautiful.

In one specific embodiment of the present application, the raw material further comprises a polymerization inhibitor, and the polymerization inhibitor accounts for 0.1 to 3%, preferably 0.2 to 2% by weight of the resin monomer.

In one specific embodiment of the present application, the polymerization inhibitor includes but not limited to any one of 2,6-di-tert-butyl-p-cresol (BHT) or t-butyl hydroquinone (TBHQ), or a combination thereof.

In one specific embodiment of the present application, the raw material further comprises a promoter, and the promoter accounts for 0.1 to 3%, preferably 0.2 to 2% by weight of the resin monomer.

In one specific embodiment of the present application, the promoter includes but not limited to any one of N,N-dimethyl-p-toluidine (DMT), N,N-dihydroxyethyl-p-toluidine (DHET), ethyl 4-dimethyl aminobenzoate (EDMAB) and N,N-dimethylamino ethylmethacrylate (DMAEMA), or a combination thereof.

In one specific embodiment of the present application, the raw material further comprises at least one of a fluorescent agent, an indicator, an inhibitor, an accelerator, a viscosity modifier, a wetting agent, an antioxidant, a surfactant, a stabilizer, and a diluent. For example, the fluorescent agent can be an azo-based fluorescent pigment, tryptophan, or a pyridine-based fluorescent pigment, and the like; the indicator can be a redox indicator or an abrasion indicator; the inhibitor can be a curing inhibitor; the accelerator can be photo-polymerization accelerator or thermal polymerization accelerator; the viscosity modifier can be paraffin wax or polyethylene wax, and the like; the wetting agent can be silane agent; the antioxidant can be sodium ascorbate and the like; the surfactant can be octylphenol polyoxyethylene ether, nonylphenol polyoxyethylene ether, high-carbon fatty alcohol polyoxyethylene ether, fatty acid polyoxyethylene ester or polyoxyethylene amine, and the like; the stabilizer can be epoxide or pentaerythritol and the like; and the diluent can be methacrylate and the like. It can be understood that the above additives are merely examples for describing the types of additives. In practical applications, additives other than exemplified above can be used, and the type of additives can also be adjusted according to actual requirements.

In one specific embodiment of the present application, the filler further comprises nanoparticle, wherein the nanoparticle accounts for 1 to 25%, preferably 1 to 15% by weight of the filler; and the average diameter of the nanoparticle is 35 to 100 nm, preferably 40 to 50 nm.

Adding nanoparticles to raw materials can give the dental materials with light transmittance and color gradients an opalescent effect close to the natural tooth.

In one specific embodiment of the present application, the raw material further includes a reinforcing fiber, and the reinforcing fiber accounts for 1 to 30%, preferably 1 to 10% by weight of the filler; the diameter of the reinforcing fiber is 0.1 to 25 μm, preferably 0.5 to 10 μm; the length of the reinforcing fiber is 0.001 to 1 mm, preferably 0.1 to 0.5 mm; and the refractive index of the reinforcing fiber is 1.4 to 1.7, preferably 1.45 to 1.6. The reinforcing fiber includes any one of glass fiber, quartz fiber, silicon fiber, ceramic fiber, and polymer fiber, or the combination thereof. The polymer fiber is preferably a polyethylene fiber.

Adding the reinforcing fiber to the raw materials can improve the fracture toughness of dental materials with light transmittance and color gradients.

In practical applications, the reinforcing fiber is subjected to cleaning and surface modification treatment before being mixed with other raw materials. The cleaning method includes heat treatment cleaning, solvent immersion cleaning or acid-base corrosion cleaning; and the modification treatment includes coupling agent modification, plasma treatment modification and chemical graft treatment modification.

The surface of the reinforcing fiber can be treated with a coupling agent. The coupling agent that can be used include but not limited to γ-methacryloyloxypropyl trimethoxysilane KH-570, γ-mercaptopropyl triethoxysilane KH-580, γ-aminopropyl trimethoxysilane JH-A111 and the like. The surface treatment of the reinforcing fiber using a coupling agent can enhance the bonding strength between the reinforcing fiber and the olefinic unsaturated monomer, thereby improving the hardness of the dental material with light transmittance and color gradients.

The surface modification of reinforcing fiber can further improve the fracture toughness of dental materials with light transmittance and color gradients.

In the embodiment of adding the reinforcing fiber to the raw materials, the raw materials other than the reinforcing fiber can be mixed and ball-milled to obtain a mixture of raw materials; and the mixture of raw materials can be mixed with the reinforcing fiber to obtain a composite resin material precursor powder. Specifically, in one specific embodiment of the present application, mixing the raw materials to obtain a composite resin material precursor powder comprises:

mixing the resin monomer, the filler, the initiator and the colorant other than the reinforcing fiber and ball milling for 0.5-2 h to obtain a mixture of raw materials, wherein the mass ratio of raw materials:grinding balls:ball milling additives is 1:1:1 to 3:6:2, preferably 2:4:1; and mixing the mixture of raw materials with the reinforcing fiber to obtain a precursor powder of composite resin materials.

In one specific embodiment of the present application, the colorant includes any one of a red colorant, a yellow colorant, and a black colorant, or a combination thereof, wherein the red colorant accounts for 0.001 to 0.06% by weight of the raw materials, and is preferably iron oxide red; the yellow colorant accounts for 0.001 to 0.04% by weight of the raw materials, and includes any one of iron oxide yellow, bismuth yellow, vanadium zirconium yellow, and cerium praseodymium yellow, or a combination thereof; and the black colorant accounts for 0 to 0.03% by weight of the raw materials, preferably iron oxide black.

In practical applications, the colorant is generally metal oxides, such as iron oxide, zirconium oxide, vanadium oxide, cerium oxide, and the like. In addition, the ratio of red colorant, yellow colorant, and black colorant can be adjusted according to different actual requirements, so as to prepare different-colorific dental materials with light transmittance and color gradients.

The present application also provides a dental material with light transmittance and color gradients prepared by using any one of the above methods.

The technical solution of the present application will be described below with reference to the specific examples. The described examples are only a part of the examples of the present application, not all of the examples.

Based on the examples of the present application, all other examples obtained by those ordinary skilled in the art without creative efforts shall fall into the scope of protection of the present application.

Table 1 shows the formulations and process parameters of four kinds of composite resin material precursor powder with different light transmittances.

TABLE 1

| Raw materials and processing conditions | | Powder 1 | Powder 2 | Powder 3 | Powder 4 |
|---|---|---|---|---|---|
| Resin monomer | Bis-GMA | 5 | 4 | 5 | — |
| | UDMA | 7 | 11 | 9 | 20 |
| | TEGDMA | 3 | 4 | 5 | 5 |
| | Bis-EMA6 | 2 | — | — | — |
| | HEMA | 2 | 1 | — | — |
| | Epoxy resin E-44 | — | — | 1 | — |
| Filler | Barium glass powder | 75 | — | 35 | 67 |
| | Lanthanum glass powder | — | 75 | 35 | — |
| | Nano-silicon oxide | 6 | — | 2 | 5 |
| | Nano-zirconium oxide | — | 5 | 3 | — |
| | Silicon oxide-zirconium oxide composite powder | — | — | 5 | — |
| | Reinforcing fiber | — | — | — | 3 |
| Initiator | Benzoyl peroxide | 0.15 | 0.2 | 0.25 | 0.3 |
| | 2,6-di-t-butyl-p-cresol | 0.25 | 0.3 | 0.2 | 0.2 |
| | N,N-dihydroxyethyl paratoluidine | 0.1 | — | 0.1 | 0.2 |
| Colorant | Iron oxide red | 0.007 | 0.021 | 0.020 | 0.042 |
| | Iron oxide yellow | 0.003 | — | 0.010 | — |
| | Bismuth yellow | — | 0.009 | — | — |
| | Cerium praseodymium yellow | — | — | — | 0.015 |
| | Iron oxide black | — | — | — | 0.003 |
| | Mass ratio of resin monomer to filler | 19/81 | 20/80 | 20/80 | 25/75 |
| Ball milling | Mass ratio of raw materials/grinding ball/ball milling additive | 2/4/1 | 3/5/1 | 2/4/1 | 1/1/1 |
| | Time (h) | 1 | 1.5 | 1.5 | 1 |
| Rotary evaporation | Temperature (° C.) | 50 | 55 | 50 | 45 |
| | Time (h) | 1.5 | 3 | 1.5 | 2 |
| Drying | Temperature (° C.) | 55 | 40 | 50 | 50 |
| | Time (h) | 5 | 3.5 | 5 | 4 |

Note:
the values corresponding to the resin monomer, filler, initiator and colorant in Table 1 are parts by weight, and each part can be 100 g.

Table 2 shows the chrominance value and light transmittance of powders 1-4 based on the Lab color system.

TABLE 2

| | Property | | | |
|---|---|---|---|---|
| Powder | Light transmittance/% | L | a | b |
| Powder 1 | 61.5 | 69.98 | −1.17 | 13.05 |
| Powder 2 | 53.3 | 69.39 | −1.10 | 14.27 |
| Powder 3 | 52.1 | 67.99 | −1.08 | 14.56 |
| Powder 4 | 46.1 | 67.64 | −0.33 | 16.60 |

The chrominance values and light transmittance of powders 1-4 are shown in Table 2. It can be seen from Table 2 that the light transmittance of powders 1-4 decreases successively. The chrominance of powders 1-4 is based on the Lab color system and is measured by a colorimeter or a spectrophotometer, after curing the powders under a preset condition. In addition, the light transmittance is measured by using a light transmittance tester at a test light wavelength of 550 nm, after curing the powders under a preset condition.

EXAMPLE 1

According to the formulations and related process parameters of powder 1, powder 2 and powder 4 in Table 1, after mixing the raw materials, powder 1, powder 2 and powder 4 with three different colors were prepared. Then powder 1 was added to the mold as the first layer and flattened. Then powder 2 was added as the second layer and flattened. Then powder 4 was added as the third layer. The thickness of powder 1 is 4 mm, the thickness of powder 2 is 6 mm, and the thickness of powder 4 is 4 mm. Then, the powder 1, powder 2 and powder 4 were molded by dry-pressing under a pressure of 4 MPa to obtain a pre-molding green body of dental material with light transmittance and color gradients. Then the pre-molding green body of dental material with light transmittance and color gradients was subjected to a thermocuring treatment, at a temperature of 115° C., a pressure of 160 MPa, and a heat-preservation time of 0.5 h, to prepare a dental material with three-layer light transmittance and color gradients.

The chrominance difference between the first layer and the third layer was 2 or more and 15 or less; the chrominance difference between the first layer and the second layer was 1 or more and 11 or less; the chrominance difference between the second layer and the third layer was 1 or more and 11 or less, and the absolute value of the chrominance difference between the first layer and the third layer minus the sum of the chrominance difference between the first layer and the second layer and the chrominance difference between the second layer and the third layer was 1 or less.

In the dental material with light transmittance and color gradients prepared by the above three kinds of powders, the light transmittance of the first layer was greater than that of the second layer; the light transmittance of the second layer was greater than that of the third layer, and the color was deepen successively from the first layer to the third layer. When a patient uses the composite resin material, the first layer will correspond to the incisal part of the tooth, and the third layer will correspond to the neck part of the tooth.

EXAMPLE 2

According to the formulations and related process parameters of powder 1, powder 3 and powder 4 in Table 1, three kinds of composite resin material precursor powders were prepared. Powder 4 was added to the mold as the first layer and flattened. Then powder 3 was added as the second layer and flattened. Then powder 1 was added as the third layer. The thickness of powder 1 is 3 mm, the thickness of powder 3 is 7 mm, and the thickness of powder 4 is 4 mm. Then, the powder 1, powder 3 and powder 4 were molded by dry-pressing under a pressure of 10 MPa to obtain a pre-molding green body of dental material with light transmittance and color gradients.

Then the pre-molding green body of dental material with light transmittance and color gradients was subjected to a thermocuring treatment, at a temperature of 131° C., a pressure of 250 MPa, and a heat-preservation time of 3 h, to prepare a dental material with three-layer light transmittance and color gradients.

The chrominance difference between the first layer and the third layer was 2 or more and 15 or less; the chrominance difference between the first layer and the second layer was 1 or more and 11 or less; the chrominance difference between the second layer and the third layer was 1 or more and 11 or less, and the absolute value of the chrominance difference between the first layer and the third layer minus the sum of the chrominance difference between the first layer and the second layer and the chrominance difference between the second layer and the third layer was 1 or less.

In the dental material with light transmittance and color gradients prepared by the above three kinds of powders, the light transmittance of the third layer was greater than that of the second layer; the light transmittance of the second layer was greater than that of the first layer, and the color was deepen successively from the third layer to the first layer. The third layer will correspond to the incisal part of the tooth, and the first layer will correspond to the neck part of the tooth.

EXAMPLE 3

According to the formulations and related process parameters of powders 1 to 4 in Table 1, four kinds of composite resin material precursor powders were prepared. Powder 1 was added to the mold as the first layer and flattened. Then powder 2 was added as the second layer and flattened. Then powder 3 was added as the third layer and flattened. Then powder 4 was added as the fourth layer. The thickness of powder 1 is 4 mm, the thickness of powder 2 is 4 mm, the thickness of powder 3 is 3 mm, and the thickness of powder 4 is 3 mm. Then, the powders 1 to 4 were molded by dry-pressing under a pressure of 20 MPa to obtain a pre-molding green body of dental material with light transmittance and color gradients.

Then the pre-molding green body of dental material with light transmittance and color gradients was subjected to a thermocuring treatment, at a temperature of 185° C., a pressure of 300 MPa, and a heat-preservation time of 4 h, to prepare a dental material with four-layer light transmittance and color gradients.

The chrominance difference between the first layer and the third layer was 2 or more and 15 or less; the chrominance difference between the first layer and the second layer was 1 or more and 11 or less; the chrominance difference between the second layer and the third layer was 1 or more and 11 or less; the chrominance difference between the third layer and the fourth layer was 1 or more and 11 or less, and the absolute value of the chrominance difference between the first layer and the fourth layer minus the sum of the chrominance difference between the first layer and the second layer, the chrominance difference between the second layer and the third layer and the chrominance difference between the third layer and the fourth layer was 1 or less.

In the dental material with light transmittance and color gradients prepared by the above four kinds of powders, the light transmittance of the first layer was greater than that of the second layer; the light transmittance of the second layer was greater than that of the third layer, the light transmittance of the third layer was greater than that of the fourth layer and the color was deepen successively from the first layer to the fourth layer. The first layer will correspond to the incisal part of the tooth, and the fourth layer will correspond to the neck part of the tooth.

In practical applications, the dental material with light transmittance and color gradients can be also prepared by the method shown in examples 4-6.

It should be noted that, four molds of 1# to 4# were used when implementing the examples 4-6. The shapes of the four molds were the same, and the volume of mold 4#>the volume of mold 3#>the volume of mold 2#>the volume of mold 1#.

EXAMPLE 4

Firstly, powder 4 was placed into the mold 1# and molded by dry-pressing under a pressure of 4 MPa to obtain a first green body. Then powder 2 was placed into the mold 2# and the first green body was placed into mold 2#, so that the first green body was coated with powder 2 and located in the middle of powder 2. The first green body and powder 2 were molded by dry-pressing under a pressure of 4 MPa to obtain a second green body. Then powder 1 was placed into the mold 4# and the second green body was placed into mold 4#, so that the second green body was coated with powder 1 and located in the middle of powder 1. The second green body and powder 1 were molded by dry-pressing under a pressure of 4 MPa to obtain a pre-molding green body of dental material with light transmittance and color gradients. Then the pre-molding green body of dental material with light transmittance and color gradients was subjected to a thermocuring treatment, at a temperature of 115° C., a pressure of 160 MPa, and a heat-preservation time of 0.5 h, to prepare a dental material with three-layer light transmittance and color gradients.

In the dental material with light transmittance and color gradients prepared in this example, powder 1 was the outermost layer, powder 2 was the secondary outer layer, and powder 4 was the innermost layer. The chrominance difference between the outermost layer and the innermost layer was 2 or more and 15 or less; the chrominance difference between the outermost layer and the secondary outer layer was 1 or more and 11 or less; the chrominance difference between the secondary outer layer and the innermost layer was 1 or more and 11 or less, and the absolute value of the chrominance difference between the outermost layer and the innermost layer minus the sum of the chrominance difference between the outermost layer and the secondary outer layer and the chrominance difference between the secondary outer layer and the innermost layer was 1 or less.

It can be understood that, in the dental material with light transmittance and color gradients prepared by example 4 of the present application, the light transmittance decreased successively from the outermost layer to the innermost layer, and the color was deepen successively from the outermost layer to the innermost layer.

EXAMPLE 5

According to the formulations and related process parameters of powder 1, powder 3 and powder 4 in Table 1, three kinds of composite resin material precursor powders were prepared. Firstly, powder 4 was placed into the mold 1# and molded by dry-pressing under a pressure of 10 MPa to obtain a first green body. Then powder 3 was placed into the mold 3# and the first green body was placed into mold 3#, so that the first green body was coated with powder 3 and located in the middle of powder 3. The first green body and powder 3 were molded by dry-pressing under a pressure of 10 MPa to obtain a second green body. Then powder 1 was placed into the mold 4# and the second green body was placed into mold 4#, so that the second green body was coated with powder 1 and located in the middle of powder 1. The second green body and powder 1 were molded by dry-pressing under a pressure of 10 MPa to obtain a pre-molding green body of dental material with light transmittance and color gradients.

Then the pre-molding green body of dental material with light transmittance and color gradients was subjected to a thermocuring treatment, at a temperature of 131° C., a pressure of 250 MPa, and a heat-preservation time of 3 h, to prepare a dental material with three-layer light transmittance and color gradients.

In the dental material with light transmittance and color gradients prepared in this example, powder 1 was the outermost layer, powder 3 was the secondary outer layer, and powder 4 was the innermost layer. The chrominance difference between the outermost layer and the innermost layer was 2 or more and 15 or less; the chrominance difference between the outermost layer and the secondary outer layer was 1 or more and 11 or less; the chrominance difference between the secondary outer layer and the innermost layer was 1 or more and 11 or less, and the absolute value of the chrominance difference between the outermost layer and the innermost layer minus the sum of the chrominance difference between the outermost layer and the secondary outer layer and the chrominance difference between the secondary outer layer and the innermost layer was 1 or less.

In the dental material with light transmittance and color gradients prepared by example 5 of the present application, the light transmittance decreased successively from the outermost layer to the innermost layer; and the color was deepen successively from the outermost layer to the innermost layer.

EXAMPLE 6

According to the formulations and related process parameters of powders 1 to 4 in Table 1, four kinds of composite resin material precursor powders were prepared. Firstly, powder 4 was placed into the mold 1# and molded by dry-pressing under a pressure of 20 MPa to obtain a first green body. Then powder 3 was placed into the mold 2# and the first green body was placed into mold of 2#, so that the first green body was coated with powder 3 and located in the middle of powder 3. The first green body and powder 3 were dry-pressed under a pressure of 20 MPa to obtain a second green body. Then powder 2 was placed into the mold of 3# and the second green body was placed into mold of 3#, so that the second green body was coated with powder 2 and at the same time the second green body was located in the middle of powder 2. The second green body and powder 2 were molded by dry-pressing under a pressure of 20 MPa to obtain a third green body. Then powder 1 was placed into the mold 4# and the third green body was placed into mold 4#, so that the third green body was coated with powder 1 and located in the middle of powder 1. The third green body and powder 1 were molded by dry-pressing under a pressure of 20 MPa to obtain a pre-molding green body of dental material with light transmittance and color gradients.

Then the pre-molding green body of dental material with light transmittance and color gradients was subjected to a thermocuring treatment, at a temperature of 185° C., a pressure of 300 MPa, and a heat-preservation time of 4 h, to prepare a dental material with four-layer light transmittance and color gradients.

The material obtained by curing powder 1 can be called as the first layer. Similarly, the material obtained by curing powder 2 can be called as the second layer; the material obtained by curing powder 3 can be called as the third layer; and the material obtained by curing powder 4 can be called as the fourth layer.

The chrominance difference between the first layer and the fourth layer was 2 or more and 15 or less; the chrominance difference between the first layer and the second layer was 1 or more and 11 or less; the chrominance difference between the second layer and the third layer was 1 or more and 11 or less; the chrominance difference between the third layer and the fourth layer was 1 or more and 11 or less, and the absolute value of the chrominance difference between the first layer and the fourth layer minus the sum of the chrominance difference between the first layer and the second layer, the chrominance difference between the second layer and the third layer and the chrominance difference between the third layer and the fourth layer was 1 or less.

In the dental material with light transmittance and color gradients prepared by example 6 of the present application, the light transmittance decreased successively from the outermost layer to the innermost layer, i.e., the light transmittance of the first layer was greater than that of the second layer; the light transmittance of the second layer was greater than that of the third layer, the light transmittance of the third layer was greater than that of the fourth layer, and the color was deepen successively from the outermost layer to the innermost layer.

COMPARATIVE EXAMPLE 7

The difference between comparative example 7 and example 1 was the pressure of thermocuring is 13 MPa, and the formulation and other various process parameters of comparative example 7 were completely same as those of example 1.

COMPARATIVE EXAMPLE 8

The difference between comparative example 8 and example 2 was the pressure of thermocuring is 16 MPa, and the formulation and other various process parameters of comparative example 8 were completely same as those of example 2.

COMPARATIVE EXAMPLE 9

The difference between comparative example 9 and example 3 was the pressure of thermocuring is 20 MPa, and the formulation and other various process parameters of comparative example 9 were completely same as those of example 3.

COMPARATIVE EXAMPLE 10

The difference between comparative example 10 and example 4 was the pressure of thermocuring is 130 MPa, and the formulation and other various process parameters of comparative example 10 were completely same as those of example 4.

COMPARATIVE EXAMPLE 11

The difference between comparative example 11 and example 5 was the pressure of thermocuring is 150 MPa, and the formulation and other various process parameters of comparative example 11 were completely same as those of example 5.

The flexural strength, compressive strength, and fracture toughness of the dental materials with light transmittance and color gradients prepared in examples 1-6 and comparative examples 7-11 were measured respectively, and the results were shown in Table 3.

The test method for flexural strength refers to YY/T 0710-2009/ISO10477-2004; the test method for compressive strength refers to ISO 4049:2009; and the test method for fracture toughness refers to ISO6872-2015.

Table 3 shows the properties of the dental materials prepared in examples 1-6 and comparative example 7-12.

TABLE 3

| Examples | Property | | |
|---|---|---|---|
| | Flexural strength/MPa | Compressive strength/MPa | Fracture toughness/MPa · $m^{1/2}$ |
| Example 1 | 248.43 ± 2.11 | 581.37 ± 32.82 | 1.68 ± 0.19 |
| Example 2 | 251.37 ± 2.84 | 592.13 ± 18.67 | 1.75 ± 0.08 |
| Example 3 | 249.46 ± 3.17 | 583.76 ± 25.17 | 1.67 ± 0.11 |
| Example 4 | 252.27 ± 3.42 | 594.07 ± 26.73 | 1.81 ± 0.14 |
| Example 5 | 259.43 ± 2.71 | 594.28 ± 36.84 | 1.82 ± 0.16 |
| Example 6 | 262.49 ± 2.63 | 593.27 ± 35.16 | 1.76 ± 0.24 |
| Comparative example 7 | 203.58 ± 1.25 | 543.04 ± 29.99 | 1.30 ± 0.24 |
| Comparative example 8 | 213.14 ± 3.65 | 557.35 ± 22.16 | 1.20 ± 0.15 |
| Comparative example 9 | 209.77 ± 2.88 | 538.24 ± 15.35 | 1.15 ± 0.16 |
| Comparative example 10 | 212.02 ± 2.43 | 550.30 ± 35.69 | 1.58 ± 0.06 |
| Comparative example 11 | 223.49 ± 3.21 | 566.45 ± 32.86 | 1.54 ± 0.14 |

As can be seen from Table 3, the flexural strength in examples 1-3 is increased from lower than about 213 MPa to more than 248 MPa, the compressive strength in examples 1-3 is increased from 557 MPa to more than 581 MPa, and the fracture toughness in examples 1-3 is increased from 1.3 MPa to more than 1.67 MPa, compared to that in comparative examples 7-9. The flexural strength, compressive strength, and fracture toughness of dental materials with light transmittance and color gradients prepared by the examples of the present application have been significantly improved, thereby improving the abrasion resistance of the material.

The flexural strength in examples 4-6 is increased from lower than 223 MPa to more than 252 MPa, the compressive strength in examples 4-6 is increased from 566 MPa to more than 593 MPa, and the fracture toughness in examples 4-6 is increased from 1.58 MPa to more than 1.76 MPa, compared to that in comparative examples 10-11. The flexural strength, compressive strength, and fracture toughness of dental materials with light transmittance and color gradients prepared by the examples of the present application have been significantly improved, thereby improving the abrasion resistance of the material.

On the other hand, in one specific embodiment of the present application, the weight ratio of the filler to the resin monomer is 31:69 to 69:31, preferably 43:57 to 62:38, and the weight of the initiator is 0.1 to 3%, preferably 0.1-2% by weight of the resin monomer, the weight of colorant is 0.001 to 0.2%, preferably 0.002 to 0.1% by weight of the total resin monomer and the filler; the pressure of the molding by dry-pressing is 11 to 19 MPa, preferably 11 to 16 MPa; the thermocuring treatment is performed at a temperature of 151 to 169° C., preferably 155 to 165° C., under a pressure of 210 to 300 MPa, preferably 240 to 290 MPa for a time period of 1.1 to 1.8 h, preferably 1.6 to 1.8 h.

The technical solutions of the present application will be described below with reference to specific examples.

Table 4 shows the formulations and process parameters of four kinds of composite resin material precursor powders with different light transmittances.

TABLE 4

| Raw materials and processing conditions | | Powder 5 | Powder 6 | Powder 7 | Powder 8 |
|---|---|---|---|---|---|
| Monomer of Polymerization | Bis-GMA | 17 | 11 | 7 | — |
| | UDMA | 23 | 30 | 20 | 22 |
| | TEGDMA | 9 | 11 | 10 | 7 |
| | Bis-EMA6 | 8 | — | — | 2 |
| | HEMA | 8 | 3 | — | — |
| | Epoxy resin E-44 | — | — | 3 | 3 |
| Filler | Barium glass powder | 29 | — | 22 | 49 |
| | Lanthanum glass powder | — | 40 | 26 | — |
| | Nano-silicon oxide | 6 | — | 3 | 11 |
| | Nano-zirconium oxide | — | 5 | 3 | — |
| | Silicon oxide-zirconium oxide composite powder | — | — | 6 | — |
| | Reinforcing fiber | — | — | — | 6 |
| Initiator | Benzoyl peroxide | 0.15 | 0.1 | 0.25 | 0.3 |
| | 2,6-di-t-butyl-p-cresol | 0.05 | 0.3 | 0.2 | 0.2 |
| | N,N-dihydroxyethyl paratoluidine | 0.1 | — | 0.1 | 0.2 |
| Colorant | Iron oxide red | 0.007 | 0.021 | 0.020 | 0.042 |
| | Iron oxide yellow | 0.003 | — | 0.010 | — |
| | Bismuth yellow | — | 0.009 | — | — |
| | Cerium praseodymium yellow | — | — | — | 0.015 |
| | Iron oxide black | — | — | — | 0.003 |
| Mass ratio of monomer of polymerization to filler | | 65/35 | 55/45 | 40/60 | 34/66 |
| Ball milling | Mass ratio of raw materials/grinding ball/ball milling additive | 2/4/1 | 3/5/1 | 2/4/3 | 1/1/1 |
| | Time (h) | 1 | 1.5 | 1.5 | 1 |
| Rotary evaporation | Temperature (° C.) | 50 | 55 | 50 | 45 |
| | Time (h) | 1.5 | 3 | 1.5 | 2 |
| Drying | Temperature (° C.) | 55 | 40 | 50 | 50 |
| | Time (h) | 5 | 3.5 | 5 | 4 |

Note:
the values corresponding to the resin monomer, filler, initiator and colorant in Table 4 are parts by weight, and each part can be 100 g.

Table 5 shows the chrominance value and light transmittance of powders 5-8 based on the Lab color system.

TABLE 5

| Powder | Property | | | |
|---|---|---|---|---|
| | Light transmittance/% | L | a | b |
| Powder 5 | 58.2 | 65.78 | −1.34 | 13.52 |
| Powder 6 | 50.3 | 61.69 | −1.26 | 15.37 |
| Powder 7 | 48.6 | 59.92 | −1.18 | 15.68 |
| Powder 8 | 43.4 | 59.27 | −0.47 | 17.83 |

The chrominance value and light transmittance of powders 5-8 are shown in Table 5. It can be seen from Table 5 that the light transmittances of powders 5-8 decrease successively. The chrominance of powders 5-8 is based on the Lab color system, and is measured by a colorimeter or a spectrophotometer after curing the powders under a preset condition. In addition, the light transmittance is measured by using a light transmittance tester at a test light wavelength of 550 nm, after curing the powders under a preset condition.

EXAMPLE 12

According to the formulations and related process parameters of powder 5, powder 6 and powder 8 in Table 4, after mixing the raw materials, powder 5, powder 6 and powder 8 with three different colors were prepared. Then powder 5 was added to the mold as the first layer and flattened. Then powder 6 was added as the second layer and flattened. Then powder 8 was added as the third layer. The thickness of powder 5 is 4 mm, the thickness of powder 6 is 6 mm, and the thickness of powder 8 is 4 mm. Then, the powder 5, powder 6 and powder 8 were molded by dry-pressing under a pressure of 11 MPa to obtain a pre-molding green body of dental material with light transmittance and color gradients. Then the pre-molding green body of dental material with light transmittance and color gradients was subjected to a thermocuring treatment, at a temperature of 155° C., a pressure of 210 MPa, and a heat-preservation time of 1.1 h, to prepare a dental material with three-layer light transmittance and color gradients.

The chrominance difference between the first layer and the third layer was 2 or more and 15 or less; the chrominance difference between the first layer and the second layer was 1 or more and 11 or less; the chrominance difference between the second layer and the third layer was 1 or more and 11 or less, and the absolute value of the chrominance difference between the first layer and the third layer minus the sum of the chrominance difference between the first layer and the second layer and the chrominance difference between the second layer and the third layer was 1 or less.

In the dental material with light transmittance and color gradients prepared by the above three kinds of powders, the light transmittance of the first layer was greater than that of the second layer; the light transmittance of the second layer was greater than that of the third layer, and the color was deepen gradually from the first layer to the third layer. When a patient uses the composite resin material, the first layer will correspond to the incisal part of the tooth, and the third layer will correspond to the neck part of the tooth.

EXAMPLE 13

According to the formulations and related process parameters of powder 5, powder 7 and powder 8 in Table 4, three kinds of composite resin precursor powders were prepared. Then powder 8 was added to the mold as the first layer and flattened. Then powder 7 was added as the second layer and flattened. Then powder 5 was added as the third layer. The thickness of powder 5 is 3 mm, the thickness of powder 7 is 7 mm, and the thickness of powder 8 is 4 mm. Then, the powder 5, powder 7 and powder 8 were molded by dry-pressing under a pressure of 16 MPa to obtain a pre-molding green body of dental material with light transmittance and color gradients.

Then the pre-molding green body of dental material with light transmittance and color gradients was subjected to a thermocuring treatment, at a temperature of 165° C., a pressure of 240 MPa, and a heat-preservation time of 1.6 h, to prepare a dental material with three-layer light transmittance and color gradients.

The chrominance difference between the first layer and the third layer was 2 or more and 15 or less; the chrominance difference between the first layer and the second layer was 1 or more and 11 or less; the chrominance difference between the second layer and the third layer was 1 or more and 11 or less, and the absolute value of the chrominance difference between the first layer and the third layer minus the sum of the chrominance difference between the first layer and the second layer and the chrominance difference between the second layer and the third layer was 1 or less.

In the dental material with light transmittance and color gradients prepared by the above three kinds of powders, the light transmittance of the third layer was greater than that of the second layer; the light transmittance of the second layer was greater than that of the first layer, and the color was deepen gradually from the third layer to the first layer. When a patient uses this dental material, the third layer will correspond to the incisal part of the tooth, and the first layer will correspond to the neck part of the tooth.

EXAMPLE 14

According to the formulations and related process parameters of powders 5 to 8 in Table 4, four kinds of composite resin precursor powders were prepared. Then powder 5 was added to the mold as the first layer and flattened. Then powder 6 was added as the second layer and flattened. Then powder 7 was added as the third layer and flattened. Then powder 8 was added as the fourth layer. The thickness of powder 5 is 4 mm, the thickness of powder 6 is 4 mm, the thickness of powder 7 is 3 mm, and the thickness of powder 8 is 3 mm. Then, the powders 5 to 8 were molded by dry-pressing under a pressure of 19 MPa to obtain a pre-molding green body of dental material with light transmittance and color gradients.

Then the pre-molding green body of dental material with light transmittance and color gradients was subjected to a thermocuring treatment, at a temperature of 169° C., a pressure of 290 MPa, and a heat-preservation time of 1.8 h, to prepare a dental material with four-layer light transmittance and color gradients.

The chrominance difference between the first layer and the third layer was 2 or more and 15 or less; the chrominance difference between the first layer and the second layer was 1 or more and 11 or less; the chrominance difference between the second layer and the third layer was 1 or more and 11 or less; the chrominance difference between the third layer and the fourth layer was 1 or more and 11 or less, and the absolute value of the chrominance difference between the first layer and the fourth layer minus the sum of the chrominance difference between the first layer and the second layer, the chrominance difference between the second layer and the third layer and the chrominance difference between the third layer and the fourth layer was 1 or less.

In the dental material with light transmittance and color gradients prepared by the above four kinds of powders, the light transmittance of the first layer was greater than that of the second layer; the light transmittance of the second layer was greater than that of the third layer, the light transmittance of the third layer was greater than that of the fourth layer and the color was deepen gradually from the first layer to the fourth layer. When a patient uses this dental material, the first layer will correspond to the incisal part of the tooth, and the fourth layer will correspond to the neck part of the tooth.

In practical applications, the dental material with light transmittance and color gradients can be also prepared by the method shown in examples 15-17.

It should be noted that, the same four molds 1# to 4# as used in examples 4-6 were used when implementing examples 15-17.

EXAMPLE 15

According to the formulations and related process parameters of powder 5, powder 6 and powder 8 in Table 4, three kinds of composite resin precursor powders were prepared. Firstly, powder 8 was placed into the mold 1# and molded by dry-pressing under a pressure of 11 MPa to obtain a first green body. Then powder 6 was placed into the mold 2# and the first green body was placed into mold 2#, so that the first green body was coated with powder 6 and located in the middle of powder 6. The first green body and powder 6 were molded by dry-pressing under a pressure of 11 MPa to obtain a second green body. Then powder 5 was placed into the mold 4# and the second green body was placed into mold 4#, so that the second green body was coated with powder 5 and located in the middle of powder 5. The second green body and powder 5 were molded by dry-pressing under a pressure of 11 MPa to obtain a pre-molding green body of dental material with light transmittance and color gradients. Then the pre-molding green body of dental material with light transmittance and color gradients was subjected to a thermocuring treatment, at a temperature of 155° C., a pressure of 210 MPa, and a heat-preservation time of 1.1 h, to prepare a dental material with three-layer light transmittance and color gradients.

In the dental material with light transmittance and color gradients prepared in this example, powder 5 was the outermost layer, powder 6 was the secondary outer layer, and powder 8 was the innermost layer. The chrominance difference between the outermost layer and the innermost layer was 2 or more and 15 or less; the chrominance difference between the outermost layer and the secondary outer layer was 1 or more and 11 or less; the chrominance difference between the secondary outer layer and the innermost layer was 1 or more and 11 or less, and the absolute value of the chrominance difference between the outermost layer and the innermost layer minus the sum of the chrominance difference between the outermost layer and the secondary outer layer and the chrominance difference between the secondary outer layer and the innermost layer was 1 or less.

In the dental material with light transmittance and color gradients prepared by example 15 of the present application, the light transmittance decreased successively from the outermost layer to the innermost layer; and the color was deepen successively from the outermost layer to the innermost layer.

EXAMPLE 16

According to the formulations and related process parameters of powder 5, powder 7 and powder 8 in Table 4, three kinds of composite resin precursor powders were prepared. Firstly, powder 8 was placed into the mold 1# and molded by dry-pressing under a pressure of 11 MPa to obtain a first green body. Then powder 7 was placed into the mold 3# and the first green body was placed into mold 3#, so that the first green body was coated with powder 7 and located in the middle of powder 7. The first green body and powder 7 were molded by dry-pressing under a pressure of 11 MPa to obtain a second green body. Then powder 5 was placed into the mold 4# and the second green body was placed into mold 4#, so that the second green body was coated with powder 5 and located in the middle of powder 5. The second green body and powder 5 were molded by dry-pressing under a pressure of 11 MPa to obtain a pre-molding green body of dental material with light transmittance and color gradients.

Then the pre-molding green body of dental material with light transmittance and color gradients was subjected to a thermocuring treatment, at a temperature of 165° C., a pressure of 240 MPa, and a heat-preservation time of 1.6 h, to prepare a dental material with three-layer light transmittance and color gradients.

In the dental material with light transmittance and color gradients prepared in this example, powder 5 was the outermost layer, powder 7 was the secondary outer layer, and powder 8 was the innermost layer. The chrominance difference between the outermost layer and the innermost layer was 2 or more and 15 or less; the chrominance difference between the outermost layer and the secondary outer layer was 1 or more and 11 or less; the chrominance difference between the secondary outer layer and the innermost layer was 1 or more and 11 or less, and the absolute value of the chrominance difference between the outermost layer and the innermost layer minus the sum of the chrominance difference between the outermost layer and the secondary outer layer and the chrominance difference between the secondary outer layer and the innermost layer was 1 or less.

In the dental material with light transmittance and color gradients prepared by example 16 of the present application, the light transmittance decreased successively from the outermost layer to the innermost layer; and the color was deepen successively from the outermost layer to the innermost layer.

EXAMPLE 17

According to the formulations and related process parameters of powders 5 to 8 in Table 4, four kinds of composite resin precursor powders were prepared. Firstly, powder 8 was placed into the mold 1# and molded by dry-pressing under a pressure of 11 MPa to obtain a first green body. Then powder 7 was placed into the mold 2# and the first green body was placed into mold 2#, so that the first green body was coated with powder 7 and located in the middle of powder 7. The first green body and powder 7 were molded by dry-pressing under a pressure of 11 MPa to obtain a second green body. Then powder 6 was placed into the mold 3# and the second green body was placed into mold 3#, so that the second green body was coated with powder 6 and located in the middle of powder 6. The second green body and powder 6 were molded by dry-pressingunder a pressure of 11 MPa to obtain a third green body. Then powder 5 was placed into the mold 4# and the third green body was placed into mold 4#, so that the third green body was coated with powder 5 and located in the middle of powder 5. The third green body and powder 5 were molded by dry-pressing under a pressure of 11 MPa to obtain a pre-molding green body of dental material with light transmittance and color gradients.

Then the pre-molding green body of dental material with light transmittance and color gradients was subjected to a thermocuring treatment, at a temperature of 169° C., a pressure of 290 MPa, and a heat-preservation time of 1.8 h, to prepare a dental material with four-layer light transmittance and color gradients.

The material obtained by curing powder 5 can be called as the first layer. Similarly, the material obtained by curing powder 6 can be called as the second layer; the material obtained by curing powder 7 can be called as the third layer; and the material obtained by curing powder 8 can be called as the fourth layer.

The chrominance difference between the first layer and the fourth layer was 2 or more and 15 or less; the chrominance difference between the first layer and the second layer was 1 or more and 11 or less; the chrominance difference between the second layer and the third layer was 1 or more and 11 or less; the chrominance difference between the third layer and the fourth layer was 1 or more and 11 or less, and the absolute value of the chrominance difference between the first layer and the fourth layer minus the sum of the chrominance difference between the first layer and the second layer, the chrominance difference between the second layer and the third layer and the chrominance difference between the third layer and the fourth layer was 1 or less.

In the dental material with light transmittance and color gradients prepared by example 17 of the present application, the light transmittance decreased successively from the outermost layer to the innermost layer, i.e., the light transmittance of the first layer was greater than that of the second layer; the light transmittance of the second layer was greater than that of the third layer, the light transmittance of the third layer was greater than that of the fourth layer and the color was deepen successively from the outermost layer to the innermost layer.

COMPARATIVE EXAMPLE 18

The difference between comparative example 18 and example 12 was the pressure of thermocuring is 13 MPa, and the formulation and other various process parameters of comparative example 18 were completely same as those of example 12.

COMPARATIVE EXAMPLE 19

The difference between comparative example 19 and example 13 was the pressure of thermocuring is 16 MPa, and the formulation and other various process parameters of comparative example 19 were completely same as those of example 13.

COMPARATIVE EXAMPLE 20

The difference between comparative example 20 and example 14 was the pressure of thermocuring is 20 MPa, and the formulation and other various process parameters of comparative example 20 were completely same as those of example 14.

COMPARATIVE EXAMPLE 21

The difference between comparative example 21 and example 15 was the pressure of thermocuring is 130 MPa, and the formulation and other various process parameters of comparative example 21 were completely same as those of example 15.

COMPARATIVE EXAMPLE 22

The difference between comparative example 22 and example 16 was the pressure of thermocuring is 150 MPa, and the formulation and other various process parameters of comparative example 22 were completely same as those of example 16.

The flexural strength, compressive strength, and fracture toughness of the dental materials with light transmittance and color gradients prepared in examples 12-17 and comparative examples 18-22 were measured respectively, and the results were shown in Table 6.

The test method for flexural strength refers to YY/T 0710-2009/ISO 10477-2004; the test method for compressive strength refers to ISO 4049:2009; and the test method for fracture toughness refers to ISO6872-2015.

Table 6 shows the properties of the dental materials with light transmittance and color gradients prepared in examples 12-17 and comparative example 18-22.

TABLE 6

| Examples | Flexural strength/MPa | Compressive strength/MPa | Fracture toughness/MPa · $m^{1/2}$ |
|---|---|---|---|
| Example 12 | 254.37 ± 1.71 | 593.74 ± 22.85 | 1.72 ± 0.11 |
| Example 13 | 255.61 ± 3.41 | 596.12 ± 16.78 | 1.74 ± 0.10 |
| Example 14 | 250.44 ± 2.84 | 591.37 ± 18.35 | 1.76 ± 0.14 |
| Example 15 | 257.31 ± 4.37 | 597.18 ± 23.64 | 1.80 ± 0.26 |
| Example 16 | 262.71 ± 7.39 | 596.43 ± 13.48 | 1.79 ± 0.12 |
| Example 17 | 269.16 ± 3.32 | 601.45 ± 16.43 | 1.78 ± 0.14 |
| Comparative example 18 | 218.35 ± 5.18 | 547.31 ± 9.91 | 1.28 ± 0.19 |
| Comparative example 19 | 214.61 ± 4.67 | 548.81 ± 12.46 | 1.24 ± 0.06 |
| Comparative example 20 | 210.61 ± 8.21 | 549.17 ± 13.42 | 1.27 ± 0.21 |
| Comparative example 21 | 208.18 ± 4.67 | 551.21 ± 14.73 | 1.27 ± 0.08 |
| Comparative example 22 | 218.49 ± 7.35 | 546.17 ± 16.92 | 1.35 ± 0.21 |

As can be seen from Table 6, the flexural strength in examples 12-14 is increased from lower than about 218 MPa to more than 250 MPa, the compressive strength in examples 12-14 is increased from 549 MPa to more than 591 MPa, and the fracture toughness in examples 12-14 is increased from 1.28 MPa to more than 1.72 MPa, compared to that in comparative examples 18-20. The flexural strength, compressive strength, and fracture toughness of dental materials with light transmittance and color gradients prepared by the examples of the present application have been significantly improved, thereby improving the abrasion resistance of the material.

The flexural strength in examples 15-17 is increased from lower than 220 MPa to more than 257 MPa, the compressive strength in examples 15-17 is increased from 553 MPa to more than 596 MPa, and the fracture toughness in examples 15-17 is increased from 1.35 MPa to more than 1.78 MPa, compared to that in comparative examples 21-22. The flexural strength, compressive strength, and fracture toughness of dental materials with light transmittance and color gradients prepared by the examples of the present application have been significantly improved, thereby improving the abrasion resistance of the material.

The above are only preferred examples of the present application, and are not intended to limit the present application. Any modification, equivalent replacement, or improvement made within the spirit and principles of the present application shall be included in the scope of the present application.

The invention claimed is:

1. A method for preparing a dental material with light transmittance and color gradients, comprising:

(1) preparing at least three kinds of composite resin material precursor powders with different light transmittances, wherein each composite resin material precursor powder with a light transmittance is prepared by:
weighing raw materials, including a resin monomer, a filler, an initiator and a colorant, wherein the filler is an inorganic material or an organic filler, and wherein the colorant includes any one of a red colorant, a yellow colorant, and a black colorant; and
mixing the raw materials to obtain a composite resin material precursor powder,
wherein the weight ratio of the filler to the resin monomer is 10:90 to 90:10, the initiator is present in an amount of 0.1 to 3% by weight of the resin monomer, the colorant is present in an amount of 0.001 to 0.2% by weight of the total resin monomer and the filler; and wherein the resin monomer includes olefinic unsaturated monomers and/or epoxy resins;

(2) adding successively the at least three kinds of composite resin material precursor powders with different light transmittances to a mold in an ascending order of light transmittance or in an descending order of light transmittance, and molding by dry-pressing under a pressure of 3 to 20 MPa, to obtain a pre-molding green body of dental material with light transmittance and color gradients; wherein a top surface of the precursor powder is flattened after adding each composite resin material precursor powder into the mold;
or (2') among the at least three kinds of composite resin material precursor powders with different light transmittances, molding by dry-pressing a composite resin material precursor powder with a first light transmittance under a pressure of 3 to 20 MPa to obtain a first green body; coating the first green body with a composite resin material precursor powder with a second light transmittance, molding by dry-pressing under a pressure of 3 to 20 MPa to obtain a second green body; and repeating the operations of coating and molding by dry-pressing until the at least three kinds of composite resin material precursor powders are molded by dry-pressing to obtain a pre-molding green body of dental material with light transmittance and color gradients, wherein the light transmittance of each layer of precursor powder in the pre-molding green body of dental material with light transmittance and color gradients is increased successively from inside to outside; and (3) subjecting the pre-molding green body of dental material with light transmittance and color gradients prepared in step (2) or step (2') to a thermocuring treatment to obtain the dental material with light transmittance and color gradients, wherein the thermocuring treatment is performed at a temperature of 151 to 169° C. under a pressure of 210 to 300 MPa for a time period of 1.1 to 1.8 h.

2. The method according to claim 1, wherein the dental material with light transmittance and color gradients further has a multi-layer color, and a chrominance difference between two adjacent layers of the composite resin materials is greater than or equal to 1 and less than or equal to 11 based on the Lab color system;
the maximum value of a chrominance difference between non-adjacent layers of the composite resin materials in the dental material with light transmittance and color gradients is greater than or equal to 2 and less than or equal to 15 based on the Lab color system;
the difference between the sum of chrominance differences between all adjacent layers of composite resin materials in the dental material with light transmittance and color gradients and the chrominance difference between the layers of composite resin materials with a highest chrominance and a lowest chrominance in the dental material with light transmittance and color gradients is not more than 2;
wherein,
an equation for calculating the chrominance difference based on the Lab color system is $\Delta E=\sqrt{\Delta L^2+\Delta a^2+\Delta b^2}$, wherein $\Delta E$ is a chrominance difference; $\Delta L$ is a difference of L values between two layers; $\Delta a$ is a difference of a values between two layers; and $\Delta b$ is a difference of b values between two layers.

3. The method according to claim 1, wherein the dental material with light transmittance and color gradients also has a multi-layer light transmittance, wherein a difference of light transmittance between two adjacent layers of the dental material with light transmittance and color gradients is 0.5 to 10%; a difference of light transmittance between two non-adjacent layers of composite resin material is 1 to 15%; and a visible-light (wavelength of 550 nm) transmittance of a layer of composite resin material with a highest light transmittance is 50 to 75%, a light transmittance of a layer of composite resin material with a lowest light transmittance is 30 to 60%, and a light transmittance of other layers of the composite resin material between the layer of composite resin material with a highest light transmittance and the layer of composite resin material with a lowest light transmittance is 40 to 70%.

4. The method according to claim 1, wherein the weight ratio of the filler to the resin monomer is 31:69 to 69:31, the initiator is present in an amount of 0.1 to 3 by weight of the resin monomer, the colorant is present in an amount of 0.001 to 0.2% by weight of the total resin monomer and the filler.

5. The method according to claim 1, wherein mixing the raw materials to obtain the composite resin material precursor powder comprises:
mixing the raw materials with a ball milling additive and ball milling for 0.5 to 2 h to obtain the composite resin material precursor powder, wherein a mass ratio of the raw materials:grinding balls:the ball milling additive is (1:1:1) to (3:6:2).

6. The method according to claim 1, wherein a particle size of the filler is not more than 2.5 μm and a refractive index of the filler is 1.40 to 1.7.

7. The method according to claim 1, wherein the raw materials further comprise a polymerization inhibitor, wherein the polymerization inhibitor accounts for 0.1 to 3% by weight of the resin monomer.

8. The method according to claim 1, wherein the raw materials further comprise a promoter, wherein the promoter accounts for 0.1 to 3% by weight of the resin monomer.

9. The method according to claim 1, wherein the raw materials further comprise at least one of a fluorescent agent, an indicator, an inhibitor, an accelerator, a viscosity modifier, a wetting agent, an antioxidant, a surfactant, a stabilizer, and a diluent.

10. The method according to claim 1, wherein the filler further comprises nanoparticles, wherein the nanoparticles account for 1 to 25% by weight of the filler; and an average diameter of the nanoparticles is 35 to 100 nm.

11. The method according to claim 1, wherein the raw materials further include reinforcing fibers, wherein the reinforcing fibers account for 1 to 30% by weight of the filler; a diameter of the reinforcing fibers is 0.1 to 25 μm; a length of the reinforcing fibers is 0.001 to 1 mm; a refractive index of the reinforcing fibers is 1.4 to 1.7; and the reinforcing fibers include any one of glass fibers, quartz fibers, silicon fibers, ceramic fibers, and polymer fibers, or a combination thereof.

12. The method according to claim 11, wherein mixing the raw materials to obtain the composite resin material precursor powder comprises:

mixing the resin monomer, the filler, the initiator and the colorant other than the reinforcing fibers, and ball milling for 0.5-2 h to obtain a mixture of raw materials, wherein the mass ratio of raw materials: grinding balls: ball milling additive is (1:1:1) to (3:6:2); and mixing the mixture of raw materials with the reinforcing fibers to obtain the composite resin material precursor powder.

13. The method according to claim 1, wherein the colorant includes any one of a red colorant, a yellow colorant, and a black colorant, or a combination thereof, wherein the red colorant accounts for 0.001 to 0.06% by weight of the raw materials; the yellow colorant accounts for 0.001 to 0.04% by weight of the raw materials, and includes any one of iron oxide yellow, bismuth yellow, vanadium zirconium yellow, and cerium praseodymium yellow, or a combination thereof; and the black colorant accounts for 0 to 0.03% by weight of the raw materials.

14. A dental material with light transmittance and color gradients produced by the method according to claim 1.

* * * * *